(12) United States Patent
Ivancic et al.

(10) Patent No.: US 9,771,541 B2
(45) Date of Patent: Sep. 26, 2017

(54) LUBRICATING COMPOSITION CONTAINING AN ASHLESS TBN BOOSTER

(71) Applicant: The Lubrizol Corporation, Wickliffe, OH (US)

(72) Inventors: Danielle N. Ivancic, Willoughby, OH (US); Christopher L. Friend, Nottingham (GB); Christopher J. Ciolli, Perry, OH (US); Scott Capitosti, Perry, OH (US); Ewan E. Delbridge, Concord Township, OH (US); William D. Abraham, Concord Township, OH (US)

(73) Assignee: The Lubrizol Corporation, Wickliffe, OH (US)

( * ) Notice: Subject to any disclaimer, the term of this patent is extended or adjusted under 35 U.S.C. 154(b) by 0 days.

(21) Appl. No.: 14/424,460

(22) PCT Filed: Aug. 19, 2013

(86) PCT No.: PCT/US2013/055517
§ 371 (c)(1),
(2) Date: Feb. 27, 2015

(87) PCT Pub. No.: WO2014/074197
PCT Pub. Date: May 15, 2014

(65) Prior Publication Data
US 2015/0225664 A1    Aug. 13, 2015

Related U.S. Application Data

(60) Provisional application No. 61/699,429, filed on Sep. 11, 2012.

(51) Int. Cl.
| | | |
|---|---|---|
| *C10M 135/02* | (2006.01) | |
| *C10M 135/28* | (2006.01) | |
| *C07C 321/28* | (2006.01) | |
| *C07C 321/26* | (2006.01) | |

(52) U.S. Cl.
CPC ......... *C10M 135/02* (2013.01); *C07C 321/26* (2013.01); *C07C 321/28* (2013.01); *C10M 135/28* (2013.01); *C10M 2203/1025* (2013.01); *C10M 2207/026* (2013.01); *C10M 2207/283* (2013.01); *C10M 2215/064* (2013.01); *C10M 2215/28* (2013.01); *C10M 2219/02* (2013.01); *C10M 2219/022* (2013.01); *C10M 2219/046* (2013.01); *C10M 2219/086* (2013.01); *C10M 2219/089* (2013.01); *C10M 2223/045* (2013.01); *C10N 2210/02* (2013.01); *C10N 2230/10* (2013.01); *C10N 2230/36* (2013.01); *C10N 2230/42* (2013.01); *C10N 2230/43* (2013.01); *C10N 2230/45* (2013.01); *C10N 2230/52* (2013.01); *C10N 2240/10* (2013.01)

(58) Field of Classification Search
CPC .............. C10M 135/02; C10M 135/28; C10M 2203/1025; C10M 2207/026; C10M 2207/283; C10M 2215/064; C10M 2215/28; C10M 2219/02; C10M 2219/022; C10M 2219/046; C10M 2219/086; C10M 2219/089; C10M 2223/045; C10N 2210/02; C10N 2230/10; C10N 2230/36; C10N 2230/42; C10N 2230/43; C10N 2230/45; C10N 2230/52; C10N 2240/10; C07C 321/26; C07C 321/28

See application file for complete search history.

(56) References Cited

U.S. PATENT DOCUMENTS

| | | |
|---|---|---|
| 2,162,207 A | 6/1939 | Moran et al. |
| 2,350,746 A | 6/1944 | Fuller et al. |
| 2,369,090 A | 2/1945 | Trautmann et al. |
| 2,376,306 A | 5/1945 | Bishop et al. |
| 2,390,943 A | 12/1945 | Kavenaugh et al. |
| 2,771,368 A | 11/1956 | Thompson et al. |
| 3,156,728 A | 11/1964 | Orloff et al. |
| 3,224,972 A * | 12/1965 | Orloff .................. C11B 5/0071 252/402 |
| 3,642,632 A | 2/1972 | Coburn et al. |
| 3,844,956 A * | 10/1974 | Nnadi ...................... C10M 1/08 252/402 |
| 3,856,690 A | 12/1974 | Braid et al. |
| 3,981,809 A | 9/1976 | Caspari et al. |
| 4,076,636 A | 2/1978 | Nnadi et al. |
| 4,234,434 A | 11/1980 | Wulfers et al. |
| 2007/0232504 A1 | 10/2007 | Goyal et al. |

(Continued)

FOREIGN PATENT DOCUMENTS

WO        2010107882 A1    9/2010

OTHER PUBLICATIONS

Written Opinion of the Corresponding International Application No. PCT/US13/055517 dated May 2, 2014.

(Continued)

*Primary Examiner* — James Goloboy
(74) *Attorney, Agent, or Firm* — Christopher D. Hilker

(57) ABSTRACT

The invention provides a lubricating composition containing an oil of lubricating viscosity and a sulfurized aromatic amine compound, especially sulfur coupled aniline. The invention further relates to methods of lubricating an internal combustion engine by supplying the described lubricating composition to the internal combustion engine. The invention further relates to the use of the sulfurized aromatic amine compound as a TBN booster and an antioxidant.

8 Claims, No Drawings

(56) References Cited

U.S. PATENT DOCUMENTS

2009/0203561 A1* 8/2009 Kamano .............. C10M 135/26
                                                          508/362
2010/0160195 A1   6/2010 Cheng et al.

OTHER PUBLICATIONS

Search Report of the Corresponding International Application No. PCT/US13/055517 dated May 2, 2014.
Corresponding International Publication No. WO/2014/074197 A1 Published May 15, 2014.

* cited by examiner

US 9,771,541 B2

LUBRICATING COMPOSITION CONTAINING AN ASHLESS TBN BOOSTER

FIELD OF INVENTION

The invention provides a lubricating composition containing a sulfurized amino-benzene compound and an oil of lubricating viscosity. The invention further relates to the use of the lubricating composition in an internal combustion engine. The invention further relates to the use of the sulfurized amino-benzene compound to deliver a basic amine to a lubricant while reducing and/or limiting detrimental effects commonly associated with basic amine additive containing lubricants, such as poor seal compatibility.

BACKGROUND OF THE INVENTION

It is known that lubricants become less effective during their use due to exposure to the operating conditions of the device they are used in, and particularly due to exposure to by-products generated by the operation of the device. For example, engine oil becomes less effective during its use, in part due to exposure of the oil to acidic and pro-oxidant byproducts. These byproducts result from the incomplete combustion of fuel in devices such as internal combustion engines, which utilize the oil. These byproducts lead to deleterious effects in the engine oil, and so, on the engine as well. The byproducts can oxidize hydrocarbons found in the lubricating oil, yielding carboxylic acids and other oxygenates. These oxidized and acidic hydrocarbons can then go on to cause corrosion, wear and deposit problems.

Base containing additives are added to lubricants in order to neutralize such byproducts, thus reducing the harm they cause to the lubricant, such as an engine oil, and so to the device, such as an engine. Over-based calcium or magnesium carbonate detergents have been used for some time as acid scavengers, neutralizing these byproducts and so protecting both the lubricant and the device. However, over-based phenate and sulfonate detergents carry with them an abundance of metal as measured by sulfated ash. New industry upgrades for diesel and passenger car lubricating oils are putting ever decreasing limits on the amount of sulfated ash, and by extension the amount of over-based detergent, permissible in an oil. A source of base that consists of only N, C, H, and O is extremely desirable.

Basic amine additives are an alternative to ash containing over-based metal detergents, in particular alkyl and aromatic amines. However, the addition of basic amine additives can lead to additional detrimental effects. For example, it is known that alkyl and some aromatic amines degrade fluoroelastomeric seals materials. These basic amine additives, such as succinimide dispersants, contain polyamine headgroups, which provide the source of base to the oil. However, such amines are believed to cause dehydrofluorination in fluoroelastomeric seals materials, such as Viton seals. This is a first step in seals degradation. Seal degradation leads to seal failure, such as seal leaks, which harms engine performance and also can cause engine damage. Generally, the base content, or total base number (TBN), of a lubricant can only be boosted modestly by such a basic amine before seals degradation becomes a significant issue, limiting the amount of TBN that can be provided by such additives.

There is a need for additives that deliver ash-free base to a lubricant without causing detrimental effects. In particular, there is need for basic amine additives that deliver ash-free base to engine oil without increasing seals degradation and/or impairing seal compatibility.

U.S. Pat. No. 2,390,943 relates to compositions comprising hydrocarbon oil and a combination of stabilizing ingredients.

U.S. Pat. Nos. 2,369,090 and 3,856,690 relate to lubricants which are stabilized against oxidative degradation.

U.S. Pat. No. 3,642,632 relates to lubricant compositions having improved resistance to deterioration under high performance conditions and is focused on gas turbine engines, such as turbojet, turboprop and turbofan engines.

U.S. Pat. No. 2,771,368 (Thompson, Nov. 20, 1956) relates to the use of N-substituted trialkoxy anilines as stabilizers for organic compounds, including fuels, mineral oils, and lubricating oils.

U.S. Pat. No. 4,234,434 (Wulfers, Feb. 14, 1979) relates to the use of dialkylanilines as stabilizers for hydrocracked oil.

WO/PCT application 2010/107882 (Preston et al., Sep. 23, 2010), relates to the use of anthranilic acid derivatives as ash-free amine-derived sources of basicity that do not cause harm to seals.

United States application 2010/0160195 (Cheng et al., Jun. 24, 2010) relates to lubricating compositions comprising derivatives of N,N-dialkylated aniline as ash-free boosters of total base number (TBN).

It has now been discovered that sulfurized aromatic amine compounds may be added to lubricants, such as engine oil, to deliver base. These additives surprisingly do not cause the harm to seal performance and corrosion that one skilled in the art would expect from such basic amine additives.

SUMMARY OF THE INVENTION

The present invention relates to sulfurized aromatic amine compounds which may be used as lubricant additives. In some embodiments these compounds may also be described as amino benzene compounds. The additives of the present invention are basic amines that supply base to a lubricant without causing harm to seal performance or metal corrosion properties. The present invention also relates to a method for neutralizing harmful acids with sulfurized amino-benzene derivatives as demonstrated by their ability to boost the TBN of fully formulated engine oils. It is known to those skilled in the art that some alkyl and aromatic amines degrade fluoroelastomeric seals material. Surprisingly, the basic amines of the current invention cause little to no harm to the seals material.

The invention further provides a method of making the described sulfurized aromatic amine compounds.

The invention further provides for compositions containing the additive described herein, and optionally further comprising a metal-containing detergent, where the TBN of the overall composition and/or the TBN delivered to the composition from the additive and the optional detergent, is greater than 6 mg KOH/g. The invention also provides for the use of the additive described herein as a TBN booster such that its addition boosts the TBN of the lubricating composition to which it is added by at least 1 mg KOH/g.

The invention further provides a method of lubricating an internal combustion engine comprising the step of: (I) supplying to the internal combustion engine the lubricating composition described herein.

The invention further provides the use of the described sulfurized aromatic amine compounds as friction modifiers, as antiwear performance additives, as extreme pressure additives, as antioxidants, as lead, tin, or copper corrosion inhibitions, as seal protectants, or as seal swell additives.

DETAILED DESCRIPTION OF THE INVENTION

Various preferred features and embodiments will be described below by way of non-limiting illustration.

The amounts of additives present in the lubricating composition disclosed herein are quoted on an oil free basis, i.e. amount of actives, unless otherwise noted.

Oils of Lubricating Viscosity

The lubricating compositions of the invention comprise an oil of lubricating viscosity. Suitable oils include both natural and synthetic oils, oil derived from hydrocracking, hydrogenation, and hydrofinishing, unrefined, refined, re-refined oils or mixtures thereof.

Unrefined oils are those obtained directly from a natural or synthetic source generally without (or with little) further purification treatment.

Refined oils are similar to the unrefined oils except they have been further treated in one or more purification steps to improve one or more properties. Purification techniques are known in the art and include solvent extraction, secondary distillation, acid or base extraction, filtration, percolation and the like.

Re-refined oils are also known as reclaimed or reprocessed oils, and are obtained by processes similar to those used to obtain refined oils and often are additionally processed by techniques directed to removal of spent additives and oil breakdown products.

Natural oils useful in making the inventive lubricants include animal oils, vegetable oils (e.g., castor oil), mineral lubricating oils such as liquid petroleum oils and solvent-treated or acid-treated mineral lubricating oils of the paraffinic, naphthenic or mixed paraffinic-naphthenic types and oils derived from coal or shale or mixtures thereof.

Synthetic lubricating oils are useful and include hydrocarbon oils such as polymerized, oligomerised, or interpolymerised olefins (e.g., polybutylenes, polypropylenes, propyleneisobutylene copolymers); poly(1-hexenes), poly(1-octenes), trimers or oligomers of 1-decene, e.g., poly(1-decenes), such materials being often referred to as poly α-olefins, and mixtures thereof; alkyl-benzenes (e.g. dodecylbenzenes, tetra-decylbenzenes, dinonylbenzenes, di-(2-ethylhexyl)-benzenes); polyphenyls (e.g., biphenyls, terphenyls, alkylated polyphenyls); diphenyl alkanes, alkylated diphenyl alkanes, alkylated diphenyl ethers and alkylated diphenyl sulphides and the derivatives, analogs and homologs thereof or mixtures thereof.

Other synthetic lubricating oils include polyol esters (such as Priolube®3970), diesters, liquid esters of phosphorus-containing acids (e.g., tricresyl phosphate, trioctyl phosphate, and the diethyl ester of decane phosphonic acid), or polymeric tetrahydrofurans. Synthetic oils may be produced by Fischer-Tropsch reactions and typically may be hydroisomerised Fischer-Tropsch hydrocarbons or waxes. In one embodiment oils may be prepared by a Fischer-Tropsch gas-to-liquid synthetic procedure as well as other gas-to-liquid oils.

Oils of lubricating viscosity may also be defined as specified in April 2008 version of "Appendix E—API Base Oil Interchangeability Guidelines for Passenger Car Motor Oils and Diesel Engine Oils", section 1.3 Sub-heading 1.3. "Base Stock Categories". In one embodiment the oil of lubricating viscosity may be an API Group II or Group III oil. In one embodiment the oil of lubricating viscosity may be an API Group I oil.

The amount of the oil of lubricating viscosity present is typically the balance remaining after subtracting from 100 wt % the sum of the amount of the compound of the invention and the other performance additives.

The lubricating composition may be in the form of a concentrate and/or a fully formulated lubricant. If the lubricating composition of the invention (comprising the additives disclosed herein) is in the form of a concentrate which may be combined with additional oil to form, in whole or in part, a finished lubricant), the ratio of the of these additives to the oil of lubricating viscosity and/or to diluent oil include the ranges of 1:99 to 99:1 by weight, or 80:20 to 10:90 by weight.

The Sulfurized Aromatic Amine Compound

The present invention provides a lubricating composition containing an oil of lubricating viscosity and an additive comprising a sulfurized aromatic amine compound.

In one embodiment the sulfurized aromatic amine compound is derived from an aromatic amine represented by formula (1):

Formula (1)

wherein $R^1$ and $R^2$ are independently hydrogen, hydrocarbyl groups for example alkyl groups of 1 to 32 carbon atoms, or organic moieties containing 2 to 32 carbon atoms and one or more heteroatoms selected from the group consisting of O, N, S, and P; n is an integer from 0 to 4, 1 to 2, or preferably 1; and $R^3$ is a hydrocarbyl group of 4 to 32 carbon atoms, wherein if n is 0 then at least one of $R^1$ and $R^2$ is not hydrogen.

In some embodiments the aromatic amine of formula (1) is a para-substituted aniline compound represented by Formula (1a):

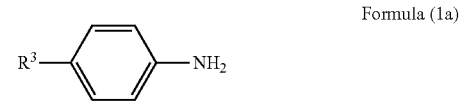

Formula (1a)

wherein $R^3$ is a linear or branched hydrocarbyl group for example an alkyl group of 4 to 32 carbon atoms. In any of the embodiments above, $R^3$ may be a hydrocarbyl group containing, at least 8 carbon atoms, at least 10 carbon atoms, or at least 12 carbon atoms. In one embodiment, $R^3$ is a linear alkyl group, i.e. includes no branch points exclusive of the point of attachment of the alkyl group to the aromatic ring. The hydrocarbyl group $R^3$ may also contain one or more branch points, and in some embodiments may contain at least 2 branch points or at least 3 or 4 branch points. In other embodiments the hydrocarbyl group $R^3$ is a fully saturated alkyl group. In still other embodiments, the hydrocarbyl group $R^3$ possesses a combination of at least two of the features discussed in this paragraph. In one embodiment, the para-substituted aniline compound used to prepare the sulfurized aromatic amine is p-dodecylaniline.

In some embodiments the aromatic amine of formula (1) is a N-substituted aniline compound represented by Formula (1b):

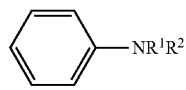

Formula (1b)

wherein $R^1$ and $R^2$ are each independently hydrogen, hydrocarbyl groups for example alkyl groups of 1 to 32 carbon atoms, or organic moieties containing 2 to 32 carbon atoms and one or more heteroatoms selected from the group consisting of O, N, S, and P; so long as $R^1$ and $R^2$ are not both hydrogen simultaneously. In some embodiments $R^1$ and $R^2$ may be linear or branched alkyl groups containing 1 to 18, 2 to 12, or 4 to 10 carbon atoms. In other embodiments $R^1$ and $R^2$ may each independently be —(CHR$^5$—CHR$^6$—O)$_m$R$^7$ or —CH$_2$CH$_2$(C=O)XR$^7$; wherein $R^5$ and $R^6$ are independently hydrogen or hydrocarbyl groups of 1 to 8, 1 to 4, or 1 to 2 carbon atoms; m is an integer from 1 to 20, 1 to 8, or 1 to 4; $R^7$ is a hydrocarbyl group of 1 to 24, 4 to 18, 6 to 16, or 8 to 12 carbon atoms; and X is oxygen (—O—), sulfur (—S—), or —NR$^8$ where $R^8$ is defined as $R^7$ above. In one embodiment, the N-substituted aniline compound used to prepare the sulfurized aromatic amine is N,N-dibutylaniline. In another embodiment, the sulfurized aromatic amine compound is derived from a combination of aromatic amines comprising amines selected from those represented by Formula (1a), Formula (1b) and mixtures thereof.

In one embodiment, the sulfurized aromatic amine compound is a sulfur-coupled aromatic amine compound, i.e. two or more aromatic amines are coupled by one or more sulfur atoms. In one embodiment the sulfurized aromatic amine compound is represented by formula (2)

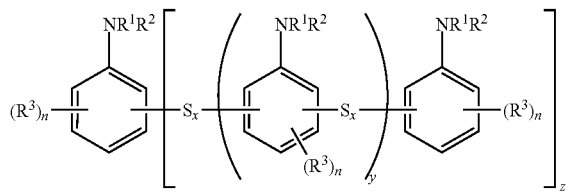

Formula (2)

wherein each $R^1$ and $R^2$ are independently hydrogen, hydrocarbyl groups for example alkyl groups of 1 to 32 carbon atoms, or organic moieties containing 2 to 32 carbon atoms and one or more heteroatoms selected from the group consisting of O, N, S, and P; n is an integer from 0 to 3; each $R^3$ is independently a hydrocarbyl group of 4 to 32 carbon atoms, wherein if n is 0 then at least one of $R^1$ and $R^2$ is not hydrogen; x is an integer from 1 to 6, or 2 to 4; y is an integer from 0 to 6; and z is an integer from 1 to 5, 1 to 4, 1 to 3, or 1 to 2. In other embodiments $R^1$, $R^2$, and $R^3$ are as defined above for formulae (1), (1a), and (1b).

In one embodiment the sulfur coupled aromatic amine compound is represented by formula (3):

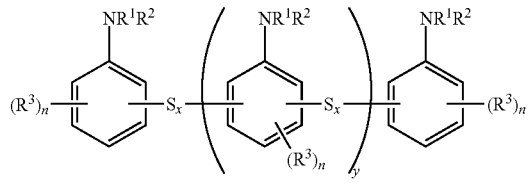

Formula (3)

wherein each $R^1$ and $R^2$ are independently hydrogen, hydrocarbyl groups for example alkyl groups of 1 to 32 carbon atoms, or organic moieties containing 2 to 32 carbon atoms and one or more heteroatoms selected from the group consisting of O, N, S, and P; n is an integer from 0 to 3; each $R^3$ is independently a hydrocarbyl group of 4 to 32 carbon atoms, wherein if n is 0 then at least one of $R^1$ and $R^2$ is not hydrogen; x is an integer from 1 to 6, or 2 to 4; and y is an integer from 0 to 6. In other embodiments $R^1$, $R^2$, and $R^3$ are as defined above for formulae (1), (1a), and (1b).

In some embodiments the aromatic amine of formula (2) is a N-substituted aniline compound represented by Formula (3a):

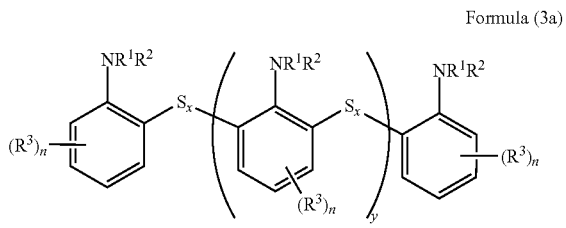

Formula (3a)

wherein $R^1$, $R^2$, $R^3$, n, x, and y are as defined for formula (3) above.

In other embodiments, the sulfurized aromatic amine compound may be described as the reaction product of an aromatic amine and sulfur, where the aromatic amine has at least one hydrocarbyl group attached directly to the aromatic ring or attached to the amine. The aromatic ring may have up to three substituent groups attached to the carbon atoms in the ring. These substituent groups may be hydrocarbyl groups. In one embodiment there are no substituent groups on the aromatic ring. In some embodiments the sulfurized aromatic amine additive of the present invention, as described by any of the formulas above, is derived from p-dodecylaniline.

The reaction of the aromatic amine and sulfur may be carried out at elevated temperatures (i.e. above ambient temperature). In some embodiments, the reaction may be carried out at a temperature between 90° C. and 220° C. In one embodiment the reaction of the aromatic amine and sulfur is carried out between 115° C. and 190° C.

Sulfurized aromatic amine compounds of the current invention may have various relative amounts of nitrogen and sulfur. In one embodiment the molar ratio of nitrogen to sulfur is 6:1 to 1:2. In another embodiment the ratio of nitrogen to sulfur is 4.5:1 to 1:1, 4.5:1 to 1.5:1, or 4:1 to 2.5:1.

The sulfurized aromatic amine compound of the invention may be present in the lubricating compositions in amounts that deliver specific amounts of TBN. TBN may be measured by several techniques; two of the most commonly used methods include ASTM D2896 and ASTM D4739. The ability of a compound to deliver TBN as measured by both D4739 and D2896 is desired. Many amines deliver TBN as measured by D2896 but not as measured by D4739. In addition, many amines which deliver TBN as measured by both tests are destructive to seals as well as increasing corrosion of certain metals, like copper. In one embodiment the sulfurized aromatic amine compound of the invention delivers TBN as measured by both ASTM D4739 and ASTM D2896. In one embodiment, the sulfurized aromatic amine has a TBN as measured by ASTM D2896 of 30 to 220, 50 to 200, 80 to 185, or at least 70, at least 95, or at least 120.

In one embodiment, the sulfurized aromatic amine compound of the invention has a TBN as measured by ASTM D4739 of 10 to 220, 25 to 195, 45 to 165 or 65 to 140. In other embodiments the TBN as measured by ASTM D4739 is at least 20% of the TBN as measured by D2896, at least 30%, at least 50%, or at least 80%. In another embodiment the ratio of the TBN as measured by D4739:D2896 is 1:1.1 to 1:5, 1:4 to 1:2, or 1:2 to 1:3.

In other embodiments, used in combination with any of the embodiments described above, the additive may be present in a lubricating composition at 0.2, 0.5, 1.0, 1.2 or 2.0 percent by weight or more. In still other embodiments, the additive is present within a range having a lower limit of 0.2, 0.5, 1.0, 1.2 or 2.0 percent by weight and an upper limit of 3.0, 4.0, 4.5 or 5.0 percent by weight.

In some embodiments, the TBN delivered by the sulfurized aromatic amine compound, alone or in combination with a conventional detergent additive, represents a TBN of at least 0.5, 1, 2, 3, or 4 of the overall TBN of the lubricating composition. That is to say, the additive of the present invention may be used as a TBN booster and can be added to a lubricating composition to increase the overall TBN of that composition. In such embodiments, the sulfurized aromatic amine additives of the present invention may increase the TBN of the compositions to which they are added by 0.5, 1, 2, 3, 4, 5 or more units. In some embodiments, the sulfurized aromatic amine additives are present in an amount sufficient to boost the TBN of the overall composition to which it is added by 0.5 to 6 units, 1 to 5 units, or 2 to 4 units.

Additional Performance Additives

The compositions of the invention may optionally comprise one or more addition performance additives. These additional performance additives may include one or more metal deactivators, viscosity modifiers, detergents, friction modifiers (other than the compound of the present invention), antiwear agents (other than the compound of the present invention), corrosion inhibitors (other than the compound of the present invention), dispersants, dispersant viscosity modifiers, extreme pressure agents, antioxidants, foam inhibitors, demulsifiers, pour point depressants, seal swelling agents, and any combination or mixture thereof. Typically, fully-formulated lubricating oil will contain one or more of these performance additives, and often a package of multiple performance additives.

In one embodiment the invention provides a lubricating composition further comprising a dispersant, an antiwear agent (other than the compound of the present invention), a dispersant viscosity modifier, a friction modifier, a viscosity modifier, an antioxidant, an overbased detergent, or a combination thereof, where each of the additives listed may be a mixture of two or more of that type of additive. In one embodiment the invention provides a lubricating composition further comprising a polyisobutylene succinimide dispersant, an antiwear agent, a dispersant viscosity modifier, a friction modifier, a viscosity modifier (typically an olefin copolymer such as an ethylene-propylene copolymer), an antioxidant (including phenolic and aminic antioxidants), an overbased detergent (including overbased sulfonates and phenates), or a combination thereof, where each of the additives listed may be a mixture of two or more of that type of additive.

In one embodiment the lubricating composition of the invention further includes an antiwear agent such as a metal dihydrocarbyl dithiophosphate (typically zinc dialkyldithiophosphate), wherein the metal dihydrocarbyl dithiophosphate contributes at least 100 ppm, or at least 200 ppm, or 200 ppm to 1000 ppm, or 300 ppm to 800 ppm, or 400 ppm to 600 ppm of phosphorus to the lubricating composition. In one embodiment, the lubricating composition is free of or substantially free of zinc dialkyldithiophosphate (ZDDP).

Suitable dispersants for use in the compositions of the present invention include succinimide dispersants. In one embodiment the dispersant may be present as a single dispersant. In one embodiment the dispersant may be present as a mixture of two or three different dispersants, wherein at least one may be a succinimide dispersant.

The succinimide dispersant may be a derivative of an aliphatic polyamine, or mixtures thereof. The aliphatic polyamine may be aliphatic polyamine such as an ethylenepolyamine, a propylenepolyamine, a butylenepolyamine, or mixtures thereof. In one embodiment the aliphatic polyamine may be ethylenepolyamine. In one embodiment the aliphatic polyamine may be selected from the group consisting of ethylenediamine, diethylenetriamine, triethylenetetramine, tetraethylenepentamine, pentaethylenehexamine, polyamine still bottoms, and mixtures thereof.

The dispersant may be a N-substituted long chain alkenyl succinimide. Examples of N-substituted long chain alkenyl succinimide include polyisobutylene succinimide. Typically the polyisobutylene from which polyisobutylene succinic anhydride is derived has a number average molecular weight of 350 to 5000, or 550 to 3000 or 750 to 2500. Succinimide dispersants and their preparation are disclosed, for instance in U.S. Pat. Nos. 3,172,892, 3,219,666, 3,316,177, 3,340,281, 3,351,552, 3,381,022, 3,433,744, 3,444,170, 3,467,668, 3,501,405, 3,542,680, 3,576,743, 3,632,511, 4,234,435, Re 26,433, and 6,165,235, 7,238,650 and EP Patent Application 0 355 895 A.

The dispersant may also be post-treated by conventional methods by a reaction with any of a variety of agents. Among these are boron compounds, urea, thiourea, dimercaptothiadiazoles, carbon disulfide, aldehydes, ketones, carboxylic acids, hydrocarbon-substituted succinic anhydrides, maleic anhydride, nitriles, epoxides, and phosphorus compounds.

The dispersant may be present at 0.01 wt % to 20 wt %, or 0.1 wt % to 15 wt %, or 0.1 wt % to 10 wt %, or 1 wt % to 6 wt % of the lubricating composition.

In one embodiment the lubricating composition of the invention further comprises a dispersant viscosity modifier. The dispersant viscosity modifier may be present at 0 wt % to 5 wt %, or 0 wt % to 4 wt %, or 0.05 wt % to 2 wt % of the lubricating composition.

Suitable dispersant viscosity modifiers include functionalized polyolefins, for example, ethylene-propylene copolymers that have been functionalized with an acylating agent such as maleic anhydride and an amine; polymethacrylates functionalized with an amine, or esterified styrene-maleic anhydride copolymers reacted with an amine. More detailed description of dispersant viscosity modifiers are disclosed in International Publication WO2006/015130 or U.S. Pat. Nos. 4,863,623; 6,107,257; 6,107,258; and 6,117,825. In one embodiment the dispersant viscosity modifier may include those described in U.S. Pat. No. 4,863,623 (see column 2, line 15 to column 3, line 52) or in International Publication WO2006/015130 (see page 2, paragraph [0008] and preparative examples are described paragraphs [0065] to [0073]).

In one embodiment the invention provides a lubricating composition which further includes a phosphorus-containing antiwear agent. Typically the phosphorus-containing antiwear agent may be a zinc dialkyldithiophosphate, or mixtures thereof. Zinc dialkyldithiophosphates are known in the art. The antiwear agent may be present at 0 wt % to 3 wt %, or 0.1 wt % to 1.5 wt %, or 0.5 wt % to 0.9 wt % of the lubricating composition.

In one embodiment the invention provides a lubricating composition further comprising a molybdenum compound. The molybdenum compound may be selected from the group consisting of molybdenum dialkyldithiophosphates, molybdenum dithiocarbamates, amine salts of molybdenum compounds, and mixtures thereof. The molybdenum compound may provide the lubricating composition with 0 to 1000 ppm, or 5 to 1000 ppm, or 10 to 750 ppm 5 ppm to 300 ppm, or 20 ppm to 250 ppm of molybdenum.

In one embodiment the invention provides a lubricating composition further comprising an overbased detergent. The overbased detergent may be selected from the group consisting of non-sulfur containing phenates, sulfur containing phenates, sulfonates, salixarates, salicylates, and mixtures thereof.

The overbased detergent may also include "hybrid" detergents formed with mixed surfactant systems including phenate and/or sulfonate components, e.g. phenate/salicylates, sulfonate/phenates, sulfonate/salicylates, sulfonates/phenates/salicylates, as described; for example, in U.S. Pat. Nos. 6,429,178; 6,429,179; 6,153,565; and 6,281,179. Where, for example, a hybrid sulfonate/phenate detergent is employed, the hybrid detergent would be considered equivalent to amounts of distinct phenate and sulfonate detergents introducing like amounts of phenate and sulfonate soaps, respectively.

Typically an overbased detergent may be sodium salts, calcium salts, magnesium salts, or mixtures thereof of the phenates, sulfur containing phenates, sulfonates, salixarates and salicylates. Overbased phenates and salicylates, typically have a total base number of 180 to 450 TBN. Overbased sulfonates typically have a total base number of 250 to 600, or 300 to 500. Overbased detergents are known in the art. In one embodiment the sulfonate detergent may be predominantly a linear alkylbenzene sulfonate detergent having a metal ratio of at least 8 as is described in paragraphs [0026] to [0037] of US Patent Application 2005065045 (and granted as U.S. Pat. No. 7,407,919). The linear alkylbenzene sulfonate detergent may be particularly useful for assisting in improving fuel economy. The linear alkyl group may be attached to the benzene ring anywhere along the linear chain of the alkyl group, but often in the 2, 3 or 4 position of the linear chain, and in some instances in predominantly in the 2 position, resulting in the linear alkylbenzene sulfonate detergent. Overbased detergents are known in the art. The overbased detergent may be present at 0 wt % to 15 wt %, or 0.1 wt % to 10 wt %, or 0.2 wt % to 8 wt %, or 0.2 wt % to 3 wt %. For example in a heavy duty diesel engine the detergent may be present at or 2 wt % to 3 wt % of the lubricating composition. For a passenger car engine the detergent may be present at 0.2 wt % to 1 wt % of the lubricating composition.

In one embodiment the lubricating composition includes an antioxidant, or mixtures thereof. The antioxidant may be present at 0 wt % to 15 wt 5, or 0.1 wt % to 10 wt %, or 0.5 wt % to 5 wt % of the lubricating composition.

Antioxidants include sulfurized olefins, alkylated diarylamines (typically alkylated phenyl naphthyl amines for example those commercially available as Irganox® L 06 from CIBA, or alkylated diphenylamines such as dinonyl diphenylamine, octyl diphenylamine, dioctyl diphenylamine), hindered phenols, molybdenum compounds (such as molybdenum dithiocarbamates), or mixtures thereof.

The hindered phenol antioxidant often contains a secondary butyl and/or a tertiary butyl group as a sterically hindering group. The phenol group may be further substituted with a hydrocarbyl group (typically linear or branched alkyl) and/or a bridging group linking to a second aromatic group. Examples of suitable hindered phenol antioxidants include 2,6-di-tert-butylphenol, 4-methyl-2,6-di-tert-butylphenol, 4-ethyl-2,6-di-tert-butylphenol, 4-propyl-2,6-di-tert-butylphenol or 4-butyl-2,6-di-tert-butylphenol, or 4-dodecyl-2,6-di-tert-butylphenol. In one embodiment the hindered phenol antioxidant may be an ester and may include, e.g., Irganox™ L-135 from Ciba. A more detailed description of suitable ester-containing hindered phenol antioxidant chemistry is found in U.S. Pat. No. 6,559,105.

Examples of additional friction modifiers include long chain fatty acid derivatives of amines, fatty esters, or epoxides; fatty imidazolines such as condensation products of carboxylic acids and polyalkylene-polyamines; amine salts of alkylphosphoric acids; fatty alkyl tartrates; fatty alkyl tartrimides; or fatty alkyl tartramides. In some embodiments the term fatty, as used herein, can mean having a C8-22 linear alkyl group.

Friction modifiers may also encompass materials such as sulfurised fatty compounds and olefins, molybdenum dialkyldithiophosphates, molybdenum dithiocarbamates, sunflower oil or monoester of a polyol and an aliphatic carboxylic acid.

In one embodiment the friction modifier may be selected from the group consisting of long chain fatty acid derivatives of amines, long chain fatty esters, or long chain fatty epoxides; fatty imidazolines; amine salts of alkylphosphoric acids; fatty alkyl tartrates; fatty alkyl tartrimides; and fatty alkyl tartramides. The friction modifier may be present at 0 wt % to 6 wt %, or 0.05 wt % to 4 wt %, or 0.1 wt % to 2 wt % of the lubricating composition.

In one embodiment the friction modifier may be a long chain fatty acid ester. In another embodiment the long chain fatty acid ester may be a mono-ester or a diester or a mixture thereof, and in another embodiment the long chain fatty acid ester may be a triglyceride.

Other performance additives such as corrosion inhibitors include those described in paragraphs 5 to 8 of U.S. application Ser. No. 05/038,319, published as WO2006/047486, octyl octanamide, condensation products of dodecenyl succinic acid or anhydride and a fatty acid such as oleic acid with a polyamine. In one embodiment the corrosion inhibitors include the Synalox® corrosion inhibitor. The Synalox® corrosion inhibitor may be a homopolymer or copolymer of propylene oxide. The Synalox® corrosion inhibitor is described in more detail in a product brochure with Form No. 118-01453-0702 AMS, published by The Dow Chemical Company. The product brochure is entitled "SYNALOX Lubricants, High-Performance Polyglycols for Demanding Applications."

Metal deactivators including derivatives of benzotriazoles (typically tolyltriazole), dimercaptothiadiazole derivatives, 1,2,4-triazoles, benzimidazoles, 2-alkyldithiobenzimidazoles, or 2-alkyldithiobenzothiazoles; foam inhibitors including copolymers of ethyl acrylate and 2-ethylhexylacrylate and copolymers of ethyl acrylate and 2-ethylhexylacrylate and vinyl acetate; demulsifiers including trialkyl phosphates, polyethylene glycols, polyethylene oxides, polypropylene oxides and (ethylene oxide-propylene oxide) polymers; pour point depressants including esters of maleic anhydride-styrene, polymethacrylates, polyacrylates or polyacrylamides may be useful.

Pour point depressants that may be useful in the compositions of the invention include polyalphaolefins, esters of maleic anhydride-styrene, poly(meth)acrylates, polyacrylates or polyacrylamides.

In different embodiments the lubricating composition may have a composition as described in the following table:

| Additive | Embodiments (wt %) | | |
|---|---|---|---|
| | A | B | C |
| Additive of Invention | 0.05 to 1 | 0.2 to 3 | 0.5 to 2 |
| Dispersant | 0.05 to 12 | 0.75 to 8 | 0.5 to 6 |
| Dispersant Viscosity Modifier | 0 or 0.05 to 5 | 0 or 0.05 to 4 | 0.05 to 2 |
| Overbased Detergent | 0 or 0.05 to 15 | 0.1 to 10 | 0.2 to 8 |
| Antioxidant | 0 or 0.05 to 15 | 0.1 to 10 | 0.5 to 5 |
| Antiwear Agent | 0 or 0.05 to 15 | 0.1 to 10 | 0.3 to 5 |
| Friction Modifier | 0 or 0.05 to 6 | 0.05 to 4 | 0.1 to 2 |
| Viscosity Modifier | 0 or 0.05 to 10 | 0.5 to 8 | 1 to 6 |
| Any Other Performance Additive | 0 or 0.05 to 10 | 0 or 0.05 to 8 | 0 or 0.05 to 6 |
| Oil of Lubricating Viscosity | Balance to 100 | Balance to 100 | Balance to 100 |

The sulfurized aromatic amine compound of the invention may be present in embodiments (D) 0.1 wt % to 8 wt %, or (E) 1 wt % to 7 wt %, or (F) 2 wt % to 6 wt % of the lubricating composition, with the amount of dispersant viscosity modifier, overbased detergent, antioxidant, antiwear agent, friction modifier, viscosity modifier, any other performance additive (excluding a dispersant) and an oil of lubricating viscosity in amounts shown in the table above for embodiments (A) to (C). The compound of invention derived from formula (1) or formula (2) may also exhibit antioxidant performance. If the compound of invention derived from formula (1) or formula (2) exhibits dispersant performance, a portion or all of the dispersant ranges quoted in embodiments (D) to (F) may be 0 wt % to 12 wt %, or 0 wt % to 8 wt % or 0 wt % to 6 wt % of the lubricating composition.

The lubricating compositions of the present invention may have an overall TBN of greater than 5, a TBN of 6, 7, 8, 9, 10 or greater. In still other embodiments the lubricating compositions of the present invention also have a sulfated ash content of less than 1.5, 1.3 or 1.0 percent by weight.

The present invention provides a surprising ability to provide relatively high TBN while maintaining the low sulfated ash levels, and other limitations, required by increasingly stringent government regulations while at the same time protecting seal performance and compatibility.

INDUSTRIAL APPLICATION

In one embodiment the invention provides a method of lubricating an internal combustion engine comprising the step of supplying to the internal combustion engine a lubricating composition as disclosed herein. Generally the lubricant is added to the lubricating system of the internal combustion engine, which then delivers the lubricating composition to the critical parts of the engine, during its operation, that require lubrication.

In one embodiment the invention provides for the use of the sulfurized aromatic amine compound, described herein, as at least one of a TBN booster, a friction modifier, an antioxidant, a dispersant, an antiwear agent, an extreme pressure agent, a lead, tin or copper (typically lead) corrosion inhibitor, a seal additive that decreases corrosion of acrylate or fluoro-elastomer seals, or a seal additive to improve seal swell performance.

The lubricating compositions described above may be utilized in an internal combustion engine. The engine components may have a surface of steel or aluminum (typically a surface of steel), and may also be coated for example with a diamond like carbon (DLC) coating.

An aluminum surface may be comprised of an aluminum alloy that may be a eutectic or hyper-eutectic aluminum alloy (such as those derived from aluminum silicates, aluminum oxides, or other ceramic materials). The aluminum surface may be present on a cylinder bore, cylinder block, or piston ring having an aluminum alloy, or aluminum composite.

The internal combustion engine may or may not have an Exhaust Gas Recirculation system. The internal combustion engine may be fitted with an emission control system or a turbocharger. Examples of the emission control system include diesel particulate filters (DPF), or systems employing selective catalytic reduction (SCR).

In one embodiment the internal combustion engine may be a diesel fuelled engine (typically a heavy duty diesel engine), a gasoline fuelled engine, a natural gas fuelled engine or a mixed gasoline/alcohol fuelled engine. In one embodiment the internal combustion engine may be a diesel fuelled engine and in another embodiment a gasoline fuelled engine.

The internal combustion engine may be a 2-stroke or 4-stroke engine. Suitable internal combustion engines include marine diesel engines, aviation piston engines, low-load diesel engines, and automobile and truck engines.

The internal combustion engine of the present invention is distinct from gas turbine. In an internal combustion engine individual combustion events which through the rod and crankshaft translate from a linear reciprocating force into a rotational torque. In contrast, in a gas turbine (may also be referred to as a jet engine) it is a continuous combustion process that generates a rotational torque continuously without translation and can also develop thrust at the exhaust outlet. These differences result in the operation conditions of a gas turbine and internal combustion engine different operating environments and stresses.

The lubricant composition for an internal combustion engine may be suitable for any engine lubricant irrespective of the sulfur, phosphorus or sulfated ash (ASTM D-874) content. The sulfur content of the engine oil lubricant may be 1 wt % or less, or 0.8 wt % or less, or 0.5 wt % or less, or 0.3 wt % or less. In one embodiment the sulfur content may be in the range of 0.001 wt % to 0.5 wt %, or 0.01 wt % to 0.3 wt %. The phosphorus content may be 0.2 wt % or less, or 0.12 wt % or less, or 0.1 wt % or less, or 0.085 wt % or less, or 0.08 wt % or less, or even 0.06 wt % or less, 0.055 wt % or less, or 0.05 wt % or less. In one embodiment the phosphorus content may be 100 ppm to 1000 ppm, or 200 ppm to 600 ppm. The total sulfated ash content may be 2 wt % or less, or 1.5 wt % or less, or 1.1 wt % or less, or 1 wt % or less, or 0.8 wt % or less, or 0.5 wt % or less, or 0.4 wt % or less. In one embodiment the sulfated ash content may be 0.05 wt % to 0.9 wt %, or 0.1 wt % to 0.2 wt % or to 0.45 wt %.

In one embodiment the lubricating composition may be an engine oil, wherein the lubricating composition may be characterized as having at least one of (i) a sulfur content of 0.5 wt % or less, (ii) a phosphorus content of 0.1 wt % or less, (iii) a sulfated ash content of 1.5 wt % or less, or combinations thereof.

EXAMPLES

The invention will be further illustrated by the following examples, which set forth particularly advantageous embodiments. While the examples are provided to illustrate the invention, they are not intended to limit it.

Additive A

Additive A (ADD A) is sulfurized p-dodecylaniline and is prepared as follows. A 1 L, four-neck, round-bottom flask is equipped with a nitrogen inlet with sub-surface sparge tube, a thermowell, a Dean-Stark trap with Friedrich condenser, and a bleach/caustic scrubber. To the flask is added dodecylaniline (200 g), followed by sulfur (59 g). the resulting slurry was heated to 105° C. at which point the slurry dissolves to form a homogeneous solution. The reaction mixture is heated to 125° C. and stirred at temperature for 1.5 hours. The reaction mixture is heated to 175° C. for 2 hours and then heated to 185° C. for 2.5 hours. The reaction mixture is cooled to ambient temperature and diluted with aqueous sodium hydroxide (50 wt %) (75 g) and an emulsion forms. The aqueous layer is separated from the non-polar brown liquid which is washed with deionized water (1×75 mL). After separation of the water layer, the brown oil is filtered to yield a red-brown oil (122.5 g). The product has a TBN as measured by ASTM D2896 of 191, a TBN as measured by ASTM D4739 of 184, and Nitrogen:Sulfur ratio (3.6:1) (mol:mol).

Additive B

Additive B (ADD B) is sulfurized N,N-dibutylaniline and is prepared as follows. A 500 mL, four-neck, round-bottom flask is equipped with a nitrogen inlet with sub-surface sparge tube, a thermowell, a Dean-Stark trap with Friedrich condenser, and a bleach/caustic scrubber. To the flask is added N,N-dibutylaniline (75.3 g), followed by sulfur (28.5 g). The reaction mixture is heated to 125° C. and stirred at temperature for 1.5 hours. The reaction mixture is heated to 175° C. for 2 hours and then heated to 185° C. for 2.5 hours. The resulting brown oil is filtered to yield a red-brown oil (63.4 g). The product has a TBN as measured by ASTM D2896 of 217, a TBN as measured by ASTM D4739 of 4.83 and, Nitrogen:Sulfur ratio (1:1.25) (mol:mol)

Additive C

Additive C (ADD C) is sulfurized 4,4'-methylenebis(N,N-dimethylaniline) and is prepared as follows. A 500 mL, four-neck, round-bottom flask is equipped with a nitrogen inlet with sub-surface sparge tube, a thermowell, a Dean-Stark trap with Friedrich condenser, and a bleach/caustic scrubber. To the flask is added 4,4'-methylenebis(N,N-dimethylaniline) (150.0 g), followed by sulfur (45.4 g). The resulting slurry was heated to 105° C. at which point the slurry dissolves to form a homogeneous solution. The reaction mixture is heated to 125° C. and stirred at temperature for 1.5 hours. The reaction mixture is heated to 175° C. for 2 hours and then heated to 185° C. for 2.5 hours. The reaction mixture is heated to 215° for 2.5 hours. The resulting brown oil is filtered to yield a red-brown oil (120.2 g). The product has a TBN as measured by ASTM D2896 of 401.2, a TBN as measured by ASTM D4739 of 18.93, and a Nitrogen:Sulfur ratio of 1.25:1 (mol:mol).

Lubricating Compositions

A series of 15W-40 engine lubricants in Group II base oil of lubricating viscosity are prepared containing the additives described above as well as conventional additives including polymeric viscosity modifier, ashless succinimide dispersant, overbased detergents, antioxidants (combination of phenolic ester and diarylamine), zinc dialkyldithiophosphate (ZDDP), as well as other performance additives as follows (Table 1). The phosphorus, sulfur and ash contents of each of the examples are also presented in the table in part to show that each example has a similar amount of these materials and so provide a proper comparison between the comparative and invention examples.

TABLE 1

Lubricating Oil Composition Formulations

| | COMP EX1 | COMP EX2 | COMP EX3 | INV EX3 | INV EX6 | INV EX7 | INV EX8 | INV EX9 |
|---|---|---|---|---|---|---|---|---|
| Base Oil | Balance to 100% | Balance to 100% | Balance to 100% | Balance to 100% | Balance to 100% | Balance to 100% | Balance to 100% | Balance to 100% |
| Dodecylaniline | 0 | 0.96 | 0 | 0 | 0 | 0 | 0 | 0 |
| N,N-dibutyl aniline | 0 | 0 | 0.73 | 0 | 0 | 0 | 0 | 0 |
| ADD A | 0 | 0 | 0 | 1.05 | 0 | 0 | 0.5 | 2.0 |
| ADD B | 0 | 0 | 0 | 0 | 1.0 | 0 | 0 | 0 |
| ADD C | 0 | 0 | 0 | 0 | 0 | 1.0 | 0 | 0 |
| Antioxidant[2] | 0.8 | 0.8 | 0.8 | 0.8 | 0.8 | 0.8 | 0.8 | 0.8 |
| Detergent[3] | 1.3 | 1.3 | 1.3 | 1.3 | 1.3 | 1.3 | 1.3 | 1.3 |
| ZDDP | 1.0 | 1.0 | 1.0 | 1.0 | 1.0 | 1.0 | 1.0 | 1.0 |
| Additional Additives[4] | 4.1 | 4.1 | 4.1 | 4.1 | 4.1 | 4.1 | 4.1 | 4.1 |
| % Phosphorus | 0.11 | 0.11 | 0.11 | 0.11 | 0.11 | 0.11 | 0.11 | 0.11 |
| % Sulfur | 0.31 | 0.31 | 0.31 | 0.31 | 0.31 | 0.31 | 0.31 | 0.31 |
| % Ash | 0.97 | 0.97 | 0.98 | 0.97 | 0.98 | 0.98 | 0.99 | 0.97 |

[1]All amounts shown above are in weight percent and are on an oil-free basis unless otherwise noted.
[2]Antioxidant includes a combination of hindered phenol ester and alkylated diarylamine
[3]Detergent is overbased calcium alkylbenzene sulfonic acid Testing The lubricating oil composition examples summarized in Table 1 are evaluated for TBN as measured by D2896 and D4739 and fluoroelastomer seals performance (DBL6674_FKM) which probes changes in seals tensile strength and rupture elongation parameters after immersion in said formulation at 150 C for 168 hrs. Additionally, PDSC (pressure differential scanning calorimetry ACEA E-5 L85-99 was used to probe antioxidancy of said formulations boosted by sulfur coupled anilines where the oxidation induction time (OIT) is reported in minutes—which represented the time after which oxygen uptake as measured by a pressure drop ceases. The longer OIT the superior antioxidancy

TABLE 2

Base Number and Seals Data

|  | COMP EX1 | COMP EX2 | COMP EX3 | INV EX3 | INV EX6 |
|---|---|---|---|---|---|
| TBN (D2896) | 7.9 | 9.4 | 9..6 | 9.7 | 9.8 |
| TBN (D4739) | 6.9 | 6.8 | 6.7 | 8.0 | 7.2 |
| SEALS |  |  |  |  |  |
| Tensile (−%) change | 32.5 | 38.0 | 38.4 | 37.8 | — |
| Rupture (−%) change | 31.5 | 57.9 | 44.6 | 55.7 | — |
| PDSC (OIT) | 88.4 | 85.6 | — | 95 | — |

Sulfurizing aniline enables more TBN, as measured by D4739, to be delivered to the formulation (6.8 aniline vs. 8.0 mg·KOH/g S-coupled aniline while delivering near identical seals performance: Tensile elongation (T/E) (%)—38; Rupture elongation (R/E) (%)—58 vs. T/E (%)—38; R/E (%)—56 for aniline vs. S-coupled aniline respectively. PDSC testing demonstrated that the formulations devoid of S-coupled aniline had OITs of 88 and 86 minutes for the baseline and 1% aniline treated formulation respectively, whilst the S-coupled aniline treated formulation (1%) had a superior OIT of 95 minutes.

Additional Lubricating Compositions

An additional series of 15W-40 engine lubricants in Group II base oil of lubricating viscosity are prepared containing the additives described above as well as conventional additives. The formulations of these examples are provided in Table 3 below.

TABLE 3

Lubricating Oil Composition Formulations

|  | COMP EX4 | INV EX10 | COMP EX5 | INV EX11 |
|---|---|---|---|---|
| Base Oil | Balance to 100% | Balance to 100% | Balance to 100% | Balance to 100% |
| ADD A | 0 | 1.36 | 0 | 1.0 |
| Sulfurized olefin | 0.38 | 0 | 0.15 | 0 |
| Antioxidant[2] | 0.85 | 0.85 | 1.25 | 1.25 |
| Detergent[3] | 1.71 | 1.71 | 2.97 | 2.97 |
| ZDDP | 0.98 | 0.98 | 0.86 | 0.86 |
| Additional Additives[4] | 5.5 | 5.5 | 5.2 | 5.2 |
| % Phosphorus | 0.11 | 0.11 | 0.10 | 0.10 |
| % Sulfur | 0.36 | 0.36 | 0.33 | 0.34 |

[1]All amounts shown above are in weight percent and are on an oil-free basis unless otherwise noted.
[2]Antioxidant includes a combination of hindered phenol ester and alkylated diarylamine
[3]Detergent is overbased calcium alkylbenzene sulfonic acid and sulfurized phenate
[4]The Additional Additives used in the examples includes a dispersant, and an antifoam agent, and includes some amount of diluent oil. The same Additive package is used in each of the examples.

Testing

The lubricating oil composition examples summarized in Table 3 are evaluated in a nitration/oxidation bench test which assesses the oxidation and nitration resistance of crankcase engine oil formulations. The formulation is treated with nitric acid and iron naphthanoate prior to administering 50 cc/min of NOx gas whilst heating to 145° C. for 22 hours. An IR spectroscopic method is used to determine degree of sample nitration and oxidation. Additionally, TBN (ASTM D2896 and D4739) and TAN (ASTM D664) are measured SOT and EOT to determine TBN retention and TAN escalation profiles.

TABLE 4

Nitration/Oxidation Performance Data

|  | COMP EX4 | INV EX10 | COMP EX5 | INV EX11 |
|---|---|---|---|---|
| RONO2 HEIGHT absorbance/cm | 21.8 | 18.3 | 22.3 | 17.8 |
| C=O AREA absorbance/cm | 19.4 | 16.8 | 21.9 | 18.6 |
| D2896_INIT mg KOH/g | 8.3 | 10.8 | 8.4 | 10.2 |
| D2896_EOT mg KOH/g | 3.4 | 4.8 | 3.5 | 4.3 |
| D4739_INIT mg KOH/g | 7.3 | 8.7 | 7 | 6.8 |
| D4739_EOT mg KOH/g | 1.2 | 2.8 | 2 | 2.6 |
| D664_INIT mg KOH/g | 2.5 | 3 | 2.4 | 2.7 |
| D664_EOT mg KOH/g | 4.6 | 4.1 | 5.8 | 4.4 |

The results show that replacement of the sulfurized olefins in two different HD 15W-40 formulations (COMP EX4 and COMP EX5) with ADD A at approximate equal sulfur (INV EX10 and INV EX11 respectively) demonstrated improved boosted TBN retention and lower nitration and oxidation profiles along with lower EOT TAN values for the inventive examples containing the S-coupled aniline (ADD A).

It is known that some of the materials described above may interact in the final formulation, so that the components of the final formulation may be different from those that are initially added. The products formed thereby, including the products formed upon employing lubricant composition of the present invention in its intended use, may not be susceptible of easy description. Nevertheless, all such modifications and reaction products are included within the scope of the present invention; the present invention encompasses lubricant composition prepared by admixing the components described above.

Each of the documents referred to above is incorporated herein by reference, as is the priority document and all related applications, if any, which this application claims the benefit of. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil, which may be customarily present in the commercial material, unless otherwise indicated. It is to be understood that the upper and lower amount, range, and ratio limits set forth herein may be independently combined. Similarly, the ranges and amounts for each element of the invention may be used together with ranges or amounts for any of the other elements.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(i) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(ii) substituted hydrocarbon substituents, that is, substituents containing non-hydrocarbon groups which, in the context of this invention, do not alter the predominantly hydrocarbon nature of the substituent (e.g., halo (especially chloro and fluoro), hydroxy, alkoxy, mercapto, alkylmercapto, nitro, nitroso, and sulphoxy);

(iii) hetero substituents, that is, substituents which, while having a predominantly hydrocarbon character, in the context of this invention, contain other than carbon in a ring or chain otherwise composed of carbon atoms.

Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A low ash lubricant composition comprising (a) an oil of lubricating viscosity and (b) a sulfurized aromatic amine compound, wherein the lubricant composition contains about 0.02% to no more than 1.2% sulfated ash, about 0.02 to about 0.12% phosphorus, and 0 to 250 ppm of molybdenum;

wherein the aromatic amine is represented by the formula

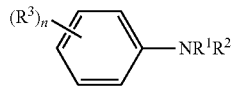

wherein $R^1$ and $R^2$ are hydrogen or alkyl groups of 1 to 32 carbon atoms, $R^3$ is a linear or branched hydrocarbyl group of at least 8 to 32 carbon atoms and n is 1 to 2; and wherein the sulfurized aromatic compound is represented by the formula

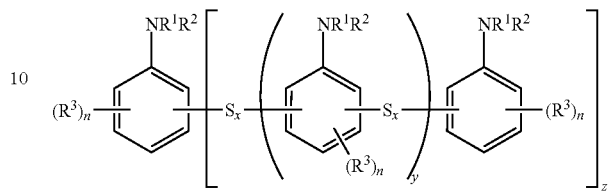

wherein:
x is an integer from 1 to 6;
y is 0; and
z is 1.

2. The lubricant composition of claim 1 wherein the sulfurized aromatic amine compound comprises the reaction product of p-dodecylaniline and a sulfurizing agent.

3. The lubricant composition of claim 1 wherein the sulfurized aromatic amine compound has a TBN of at least 30 as measured by ASTM D2896.

4. The lubricant composition of claim 1 wherein the sulfurized aromatic amine compound is present in an amount 0.05 to 5% by weight.

5. The lubricant composition of claim 1 wherein the composition further comprises a metal containing overbased detergent in an amount to deliver at least 2 TBN to the composition.

6. A method for boosting the TBN of a low ash lubricating composition without increasing the ash content of said composition, said method comprising adding to the lubricant a sulfurized aromatic amine compound of claim 1 in an amount sufficient to deliver at least 0.2 TBN.

7. A method of making a sulfurized aromatic amine compound comprising the step of (1) reacting an aromatic amine and a sulfurizing agent,
resulting in the sulfurized aromatic amine compound of claim 1.

8. A method of lubricating an internal combustion engine comprising the step of (1) supplying to the internal combustion engine the lubricant composition of claim 1.

\* \* \* \* \*